(12) United States Patent
Papke

(10) Patent No.: US 6,852,741 B2
(45) Date of Patent: Feb. 8, 2005

(54) COMPOSITIONS AND METHODS FOR TREATMENT OF NEUROLOGICAL DISORDERS

(75) Inventor: Roger L. Papke, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 10/036,988

(22) Filed: Dec. 31, 2001

(65) Prior Publication Data

US 2003/0139387 A1 Jul. 24, 2003

(51) Int. Cl.$^7$ .......................... A61K 31/44; A61K 31/55

(52) U.S. Cl. .................. 514/343; 514/214.01; 514/215; 514/290; 514/357; 514/339

(58) Field of Search .......................... 514/343, 214.01, 514/215, 290, 357, 339

(56) References Cited

U.S. PATENT DOCUMENTS

| | | | |
|---|---|---|---|
| 5,212,188 A | 5/1993 | Caldwell et al. | |
| 5,597,919 A | 1/1997 | Dull et al. | |
| 5,726,316 A | 3/1998 | Crooks et al. | |
| 5,885,998 A | 3/1999 | Bencherif et al. | |
| 5,977,144 A | 11/1999 | Meyer et al. | |
| 6,218,383 B1 * | 4/2001 | Bencherif | 514/214.01 |
| 6,224,897 B1 * | 5/2001 | Reitberg | 424/443 |
| 6,277,855 B1 | 8/2001 | Yerxa | |

FOREIGN PATENT DOCUMENTS

| | | | |
|---|---|---|---|
| WO | WO 200182978 A2 * | 11/2001 | A61K/51/04 |

OTHER PUBLICATIONS

"Radiosynthesis and PET studies of [11C]RJR–2403, a nicotinic agonist", Studenov et al., abstract, Journal of Labelled Compounds & Radiopharmaceuticals, 2001, 44(6), 425–436.*

"Nicotinic treatment of Alzheimer's disease", Newhouse et al., Society of Biological Psychiatry, 2001, 49:268–278.*

Adler, L.E. et al. "Normalization by Nicotine of Deficient Auditory Sensory Gating in the Relatives of Schizophrenics" *Biol. Psychiatry*, 1992, 32:607–616.

Adler, L.E. et al. "Normalization of Auditory Physiology by Cigarette Smoking in Schizophrenic Patients" *Am. J. Psychiatry*, 1993, 150:1856–1861.

Adler, L.E. et al. "Schizophrenia, Sensory Gating, and Nicotinic Receptors" *Schizophr. Bull.*, 1998, 24(2):189–202.

Arneric, S.P. et al. "Neuronal Nicotinic Acetylcholine Receptors" *Psychopharmacology: The Fourth Generation of Progress*, 1995, pp. 95–110.

Bencherif, F. et al. "RJR–2403: A Nicotinic Agonist with CNS Selectivity I. In Vitro Characterization" *J. Pharmacol. Exp. Ther.*, 1996, 279:1413–1421.

Benowitz, N.L. "Pharmacology of Nicotine: Addiction and Therapeutics" *Annu. Rev. Pharmacol. Toxicol.*, 1996, 36:597–613.

Cosford, N.D.P. et al. "(S)–(–)–5–Ethynyl–3–(1–methyl–2–pyrrolidinyl) pyridine Maleate (SIB–1508Y): A Novel Anti–Parkinsonian Agent with Selectivity for Neuronal Nicotinic Acetylcholine Receptors" *J. Med. Chem.*, 1996, 39:3235–3237.

Cosford, N.D.P. et al. "Recombinant human receptors and functional assays in the discovery of altinicline (SIB–1508Y), a novel acetylcholine–gated ion channel (nAChR) agonist" *Pharm. Acta. Helv.*, 2000, 74:125–130.

Damaj, M.I. et al. "Antinociceptive and Pharmacological Effects of Metanicotine, a Selective Nicotinic Agonist" *J. Pharmacol. Exp. Ther.*, 1999, 291(1):390–398.

De Fiebre, C.M. et al., "Characterization of a Series of Anabaseine–Derived Compounds Reveals that the 3–(4)–Dimethylaminocinnamylidine Derivative is a Selective Agonist at Neuronal Nicotinic $\alpha 7/^{125}$I–$\alpha$–Bungarotoxin Receptor Subtypes" *Mol. Pharmacol.*, 1995, 47:164–171.

Donnelly–Roberts, D.L. et al. "ABT–594 [(R)–5–(2–Azetidinylmethoxy)–2–Chloropyridine]: A Novel, Orally Effective Analgesic Acting via Neuronal Nicotine Acetylcholine Receptors: I. In Vitro Characterization" *J. Pharmacol. Exp. Ther.*, 1998, 285:777–786.

Flores, C.M. et al. "A Subtype of Nicotinic Cholinergic Receptor in Rat Brain is Composed of $\alpha 4$ and $\beta 2$ Subunits and is Up–regulated by Chronic Nicotine Treatment" *Mol. Pharmacol.*, 1992, 41:31–37.

Freedman, R. et al. "Schizophrenia and Nicotinic Receptors" *Harvard Rev. Psychiatry*, 1994, 2(4):179–192.

Freedman, R. et al. "The $\alpha 7$–nicotinic acetylcholine receptor and the pathology of hippocampal interneurons in schizophrenia" *J. of Chemical Neuroanatomy*, 2000, 20:299–306.

Gerzanich, V. et al. "$\alpha 5$ Subunit Alters Desensitization, Pharmacology, $Ca^{++}$Permeability and $Ca^{++}$Modulation of Human Neuronal $\alpha 3$ Nicotinic Receptors" *J. Pharmacol. Exp. Ther.*, 1998, 286(1):311–320.

(List continued on next page.)

Primary Examiner—Vickie Kim
Assistant Examiner—Brian-Yong S. Kwon
(74) Attorney, Agent, or Firm—Saliwanchik, Lloyd & Saliwanchik

(57) ABSTRACT

The present invention concerns methods for treating or preventing neurological disorders characterized by dysfunction of nicotinic acetylcholine receptors by co-administration of metanicotine and at least one compound which exhibits antagonist activity, or both agonistic and antagonists activity, toward one or more nicotinic acetylcholine receptor subtypes. The subject invention, in another aspect, pertains to pharmaceutical compositions containing metanicotine and at least one compound which inhibits antagonistic activity, or both agonistic and antagonistic activity, toward one or more nicotinic acetylcholine receptor subtypes.

7 Claims, 6 Drawing Sheets

OTHER PUBLICATIONS

Halvorsen, S.W. and D.K. Berg "Subunit Composition of Nicotinic Acetylcholine Receptors from Chick Ciliary Ganglia" *J. Neurosci.*, Jun. 1990, 10(6):1711–1718.

Holladay, M.W. et al. "Neuronal Nicotinic Acetylcholine Receptors as Targets for Drug Discovery" *J. Med. Chem.*, Dec. 19, 1997, 40(26):4169–4194.

Lippiello, P.M. et al. "RJR–2403: A Nicotinic Agonist with CNS Selectivity II. In Vivo Characterization" *J. Pharmacol. Exp. Ther.*, 1996, 279:1422–1429.

Lloyd, G.K. et al. "The Potential of Subtype–Selective Neuronal Nicotinic Acetylcholine Receptor Agonists as Therapeutic Agents" *Life Sciences*, 1998, 62(17/18):1601–1606.

Lloyd, G.K. and M. Williams "Neuronal Nicotinic Acetylcholine Receptors as Novel Drug Targets" *J. Pharmacol.*, 2000, 292(2):461–467.

Meyer, E.M. et al. "3–[2,4–Dimethoxybenzylidene]anabaseine (DMXB) selectively activates rat $\alpha 7$ receptors and improves memory–related behaviors in a mecamylamine–sensitive manner" *Brain Res.*, 1997, 768:49–56.

Mihailescu, S. and R. Drucker–Colin "Nicotine, Brain Nicotinic Receptors, and Neuropsychiatric Disorders" *Arch. Med. Res.*, 2000, 31:131–144.

Miller, C. "Genetic Manipulation of Ion Channels: A New Approach to Structure and Mechanism" *Neuron*, 1988, 2:1195–1205.

Mulle, C. et al. "Existence of Different Subtypes of Nicotinic Acetylcholine Receptors in the Rat Habenulo–interpeduncular System" *J. Neurosci.*, Aug. 1991, 11(8):2588–2597.

Newhouse, P.A. et al. "Nicotinic System Involvement in Alzheimer's and Parkinson's Diseases" *Drugs Aging*, Sep. 1997, 11(3):206–228.

Newhouse, P.A. and M. Kelton "Nicotinic systems in central nervous systems disease: degenerative disorders and beyond" *Pharm. Acta. Helv.*, 2000, 74:91–101.

Papke, R.L. "The Kinetic Properties of Neuronal Nicotinic Receptors: Genetic Basis of Functional Diversity" *Prog. Neurobiol.*, 1993, 41:509–531.

Papke, R.L. "Activation and inhibition of rat neuronal nicotinic receptors by ABT–418" *Br. J. Pharmacol.*, 1997, 120:429–438.

Papke, R.L. et al. "The Activation and Inhibition of Human Nicotinic Acetylcholine Receptor by RJR–2403 Indicate a Selectivity for the $\alpha 4\beta 2$ Receptor Subtype" *J. Neurochem.*, 2000, 75:204–216.

Papke, R.L. et al. "$\alpha 7$ Receptor–selective agonists and modes of $\alpha 7$ receptor activation" *Eur. J. Pharmacol.*, 2000, 393:170–195.

Papke, R.L. et al. "Inhibition of Wild–Type and Mutant Neuonal Nicotinic Acetylcholine Receptors by Local Anesthetics" *Mol. Pharm.*, 2001, 60:1365–1374.

Rusted, J.M. and P.A. Newhouse "Nicotinic treatment for degenerative neuropsychiatric disorders such as Alzheimer's disease and Parkinson's disease" *Behav. Brain. Res.*, 2000 113:121–129.

Sanberg, P.R. et al. "Treatment of Tourette's syndrome with mecamylamine" *Lancet*, Aug. 29, 1998, 352:705–706.

Silver, A.A. et al. "Case Study: Long–Term Potentiation of Neuroleptics with Transdermal Nicotine in Tourette's Syndrome" *J. Am. Acad. Child Adolesc. Psychiatry*, Dec. 1996, 35:1631–1636.

Sullivan, J.P. et al. "ABT–089 [2–Methyl–3(2–(S)–pyrrolidinylmethoxy)pyridine]: I. A Potent and Selective Cholinergic Channel Modulator with Neuroprotective Properties" *J. Pharmacol. Exp. Ther.*, 1997, 283(1):235–246.

Vernier, J. et al. "4–[[2–(1–Methyl–2–pyrrolidinyl)ethyl]thio]–phenol Hydrochloride (SIB–1553A): A Novel Cognitive Enhancer with Selectivity for Neuronal Nicotinic Acetylcholine Receptors" *J. Med. Chem.*, 1999, 42:1684–1686.

Vidal, C. "Nicotinic Receptors in the Brain" *Mol. Chem. Neuropathol.*, 1996, 28:3–11.

Wang, F. et al. "Assembly of Human Neuronal Nicotinic Receptor $\alpha 5$ Subunits with $\alpha 3$, $\beta 2$, and $\beta 4$ Subunits" *J. Biol. Chem.*, Jul. 1996, 271(30):17656–17665.

Webster, J.C. et al. "Antagonist activities of mecamylamine and nicotine show reciprocal dependence on beta subunit sequence in the second transmembrane domain" *Br. J. of Pharmacol.*, 1999, 127:1337–1348.

Whiting, P.J. and J.M. Lindstrom "Purification and Characterization of a Nicotinic Acetylcholine Receptor from Chick Brain" *Biochemistry*, 1986, 25:2082–2093.

Williams, M. et al. "Neuronal Nicotinic Acetylcholine Receptors" *Drug News Perspect.*, May 1994, 7(4):205–223.

Young, J.M. et al. "Mecomylamine: New Therapeutic Uses and Toxicity/Risk Profile" *Clin. Ther.*, 2001, 23(4):532–565.

\* cited by examiner

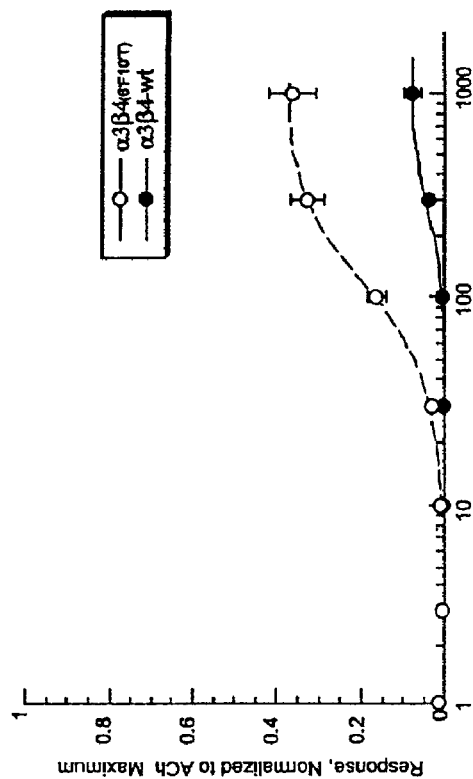
FIG. 3A
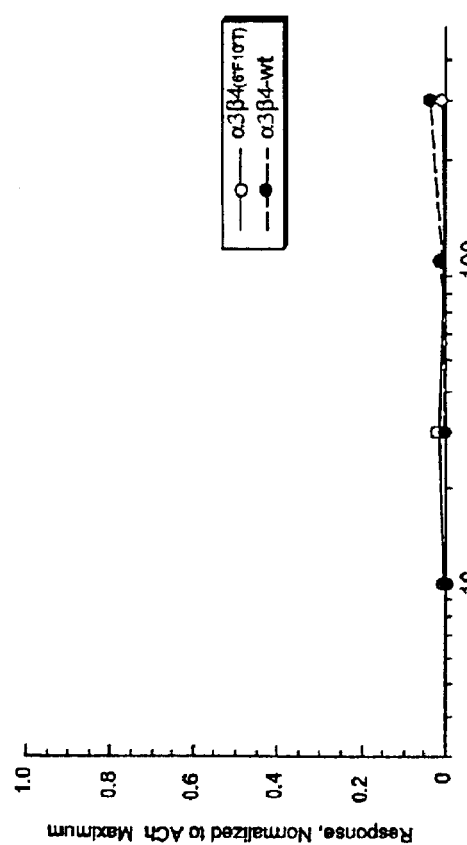
FIG. 3B
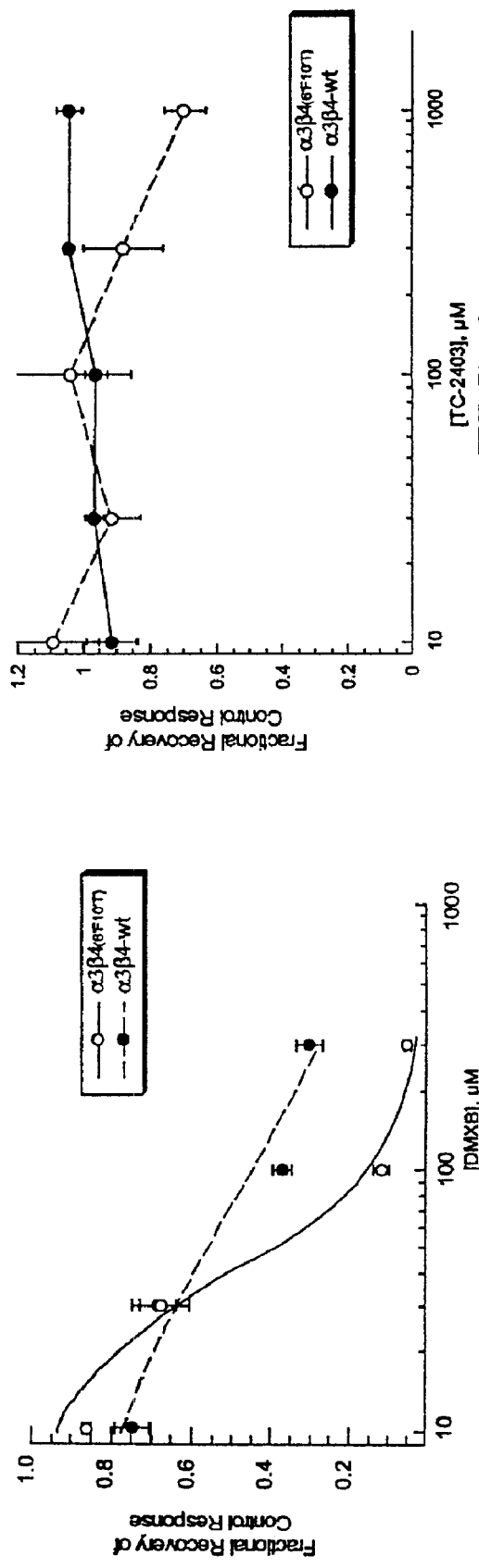
FIG. 3C
FIG. 3D

COMPOSITIONS AND METHODS FOR TREATMENT OF NEUROLOGICAL DISORDERS

The subject invention was made with government support under a research project supported by National Institutes of Health Grant No. PO1 AG10485. The government has certain rights in this invention.

BACKGROUND OF THE INVENTION

The nicotinic acetylcholine receptors (nAChRs) are members of a superfamily of ligand-gated ion channels that mediate fast signal transmission at synapses. The ion channel is formed from the assembly of a membrane protein oligomer (a pentamer) that binds the neurotransmitter, acetylcholine, its natural ligand. The nAChR also binds agonists, such as nicotine, and nicotinic antagonists, such as mecamylamine. The binding of two molecules of acetylcholine or nicotine to the alpha subunits of the receptor induces a conformational change, stabilizing the receptor's open-state, which allows the flux of ions (e.g., sodium, calcium, potassium) across the cell membrane. An influx may cause membrane depolarization and the activation of voltage-gated ion channels for sodium and calcium, resulting in the exocytotic release of neurotransmitters and hormones from vesicular stores. The overall conductance as well as the relative conductances of various ions depend on the subunit composition of the receptor (Lindstrom et al., *Ann. NY Acad. Sci.* [1995] 757:100–116; McGehee and Role, *Annu. Rev. Physiol.* [1995] 57:521–546). Nicotinic receptors are found in both muscle and neuronal tissues and are therefore broadly classified as either muscle-type or neuronal nicotinic AChRs.

There are multiple types of nAChRs in the brain associated with synaptic function, signal processing or cell survival. The therapeutic targeting of nicotinic receptors in the brain requires the identification of drugs that may be selective for their ability to activate or inhibit a limited range of these receptor subtypes.

Brain nicotinic receptor systems have long been associated with addiction. Recently, it has been shown that nicotinic receptor systems may be involved with Tourette's syndrome (Silver, A. A. et al., *J. Am. Acad. Child Adolesc. Psychiatry* [1996] 35:1631–1636; Sanberg, P. R. et al., *Lancet* [1998] 352:705–706) and schizophrenia (Adler, L. E. et al., *Biol. Psychiatry* [1992] 32:607–616, Adler, L. E. et al. *Am. J. Psychiatry* [1993] 150:1856–1861; Leonard, S. et al, *Soc. Neurosci. Abstr.* [1993] 19:837; Freedman, R. et al., *Harvard Rev. Psychiatry* [1994] 2:179–192) and that nicotinic drugs may also have applications as analgesics and for the treatment of Alzheimer's disease (Williams, M. et al., *Drug News Perspect.* [1994] 7:205–223; Arneric, S. P. et al., *Psychopharmacology: The Fourth Generation of Progress* [1995], pp. 95–110). With these newly defined therapeutic endpoints, the challenge becomes understanding how best to target nicotinic drugs to the receptor systems of the brain.

The pharmacology of neuronal nicotinic receptors, however, is very complex. With a gene family that includes at least nine different a subunits (designated $\alpha 2-\alpha 10$) that in some cases may function as homooligomers ($\alpha 7-\alpha 10$) or alternatively combine with different neuronal $\beta$ subunits ($\beta 2-\beta 4$), there is a great potential for structural diversity just on the level of the basic pentamer receptor subunit combinations (Papke, R. L. *Prog. Neurobiol.* [1993] 41:509–531). Multiple receptor subtypes are commonly found on single neurons, and single tissues have multiple neuronal cell types that differ in the function of their nicotinic receptors (Mulle, C. et al., *J. Neurosci.* [1991] 11:2588–2597).

One approach for sorting out significant elements in this complex system is to study cloned receptor subunits in defined combinations. The co-expression of $\alpha 4$ and $\beta 2$ subunits represents one receptor subunit combination of particular interest, as the primary high-affinity nicotinic receptor of the brain is composed of these subunits (Whiting, P. J. and J. M. Lindstrom, *Biochemistry* [1986] 25:2082–2093; Flores, C. M. et al., *Mol Pharmacol.* [1992] 41:31–37). Receptors containing the $\alpha 3$ subunit are also likely to be found in the brain but predominate in the peripheral nervous system (Halvorsen, S. W. and D. K. Berg, *J. Neurosci.* [1990] 10:1711–1718). The properties of both brain and ganglionic nicotinic ACh receptor (nAChR) can be modified by the co-assembly with the nonessential $\alpha 5$ subunit (Conroy, W. G. et al., Neuron. [1992] 9:679–691; Wang, F. et al., *J. Biol. Chem.* [1996] 271:17656–17665; Gerzanich, V. et al., *J. Pharmacol. Exp. Ther.* [1998] 286:311–320). Another important type of brain nicotinic receptor subtype are those that bind $\alpha$-bungarotoxin with high affinity. These receptors correspond to the $\alpha 7$ subunit gene products, which form homomeric receptors with high calcium permeability and fast desensitization to high concentrations of agonist.

Furthermore, nicotinic receptor subunits exhibit considerable promiscuity in their ability to coassemble to form functional channels in various expression systems. Therefore, it is possible that alternative subunit combinations may result under certain conditions (e.g., tissue injury, chronic drug exposure). By recombinant expression study with specific combinations of receptor subunits, the relative efficacy and potency of available nicotinic agonists and antagonists have been defined (Brioni et al., *Adv. Pharmacol.* [1997] 37:153–214; Holladay et al., *J. Med. Chem.* [1997] 40:4169–4194; Lloyd and Williams, *J. Pharmacol.* [2000] 292:461-467). Therefore, there would seem an opportunity for developing drugs that have greatly increased selectivity with respect to receptor subtype specificity. Unfortunately, subtype selective agonists and antagonists have been only slowly forthcoming.

Many of the experimental new nicotinic agents being considered for clinical development, including GTS-21, ABT-418, ABT-089, and SIB-1553A (Meyer et al., Brain Res. [1997] 768:49–56; Papke et al., *Br. J. Pharmacol.* [1997] 120:429–438; Sullivan et al., *J. Pharmacol. Exp. Ther.* [1997] 283:235–246; Lloyd et al., *Life Sci.* [1998] 62:1601–1606), have very mixed profiles of agonist and antagonist activity, meaning that each agent has both excitatory and inhibitory effects on nicotinic receptors in the brain. This mixed pharmacological profile is also observed in the prototypic cholinergic ion channel agonist, nicotine. Unfortunately, because of their mixed agonist/antagonist profiles, the toxic side effects produced by these agents hinder their development as therapeutic drugs.

Accordingly, considerable need exists for agents which selectively target nicotine acetylcholine receptors and individual receptor subtypes (i.e., receptor subunit combinations), and which avoid the toxic side effects associated with the administration of compounds that are mixed activators and inhibitors of nicotine acetylcholine receptors.

BRIEF SUMMARY OF THE INVENTION

The subject invention arose out of the discovery that when metanicotine (also known as TC-2403, RJR-2403, and (E)-N-methyl-4-(3-pyridinyl)-3-butene-1-amine) is co-administered with a compound that both activates and inhibits one or more types of nicotine acetylcholine receptors (nAChRs), metanicotine will protect nicotinic acetylcholine receptor (nAChR) function from the inhibitory effects of the compound.

The subject invention concerns methods of treating a patient suffering from a neurological condition characterized by the dysfunction of nAChRs by the co-administration of a metanicotine, or a pharmaceutically acceptable salt or analogue thereof, and a compound having either: (1) an antagonist profile of action toward one or more nAChR subtypes; or (2) a mixed agonist/antagonist profile of action toward one or more nAChR subtypes. The metanicotine and the nAChR antagonist or mixed nAChR agonist/antagonist can be simultaneously administered or consecutively administered. If administered simultaneously, the metanicotine and the nAChR antagonist, or the metanicotine and the mixed nAChR agonist/antagonist, can be administered as separate compounds, or administered together as a pharmaceutical composition of the subject invention. Therefore, in another aspect, the subject invention also pertains to pharmaceutical compositions containing metanicotine, or a pharmaceutically acceptable salt or analogue thereof, and an nAChR antagonist or mixed nAChR agonist/antagonist. The combination of nicotinic receptor ligands, incorporating metanicotine and a mixed agonist/antagonist or metanicotine and an nAChR antagonist, results in the reduction or elimination of undesirable effects that would otherwise be associated with administration of the mixed agonist/antagonist alone or the antagonist alone. This innovative approach facilitates the development of therapies for a number of neurological disorders, with improved selectivity for nAChR subtypes. Thus, the methods of the subject invention provide a therapeutic window for utilization of such nAChR antagonists or mixed agonists/antagonists in the treatment of neurological conditions where one previously did not exist.

Preferably, the methods and compositions of the subject invention are administered to treat a patient suffering from a neurological disorder associated with dysfunction of one or more subtypes of neuronal nAChR. Neurological disorders which can be treated with pharmaceutical compositions of the present invention, and in accordance with methods of the present invention, include, but are not limited to, presenile dementia (early onset Alzheimer's disease), senile dementia (dementia of the Alzheimer's type), Parkinsonism including Parkinson's disease, Huntington's chorea, tardive dyskinesia, hyperkinesias, mania, attention deficit disorder, attention deficit hyperactivity disorder, sleep-wake disorder, chronic-fatigue syndrome, tremor, epilepsy, neuropathic pain, addiction (e.g., nicotine addiction), anxiety, dyslexia, schizophrenia, obsessive-compulsive disorder, and Tourette's syndrome.

Metanicotine is an effective activator of the $\alpha 4\beta 2$ neuronal nAChR subtype, with activity comparable with that of acetylcholine (ACh) (Bencherif, M. et al., *J. Pharmacol. Exp. Ther.* [1996] 279:1413–1421; Lippiello, P. M. et al., *J. Pharmacol. Exp. Ther.* [1996] 279:1422–1429). Furthermore, metanicotine can be distinguished from nicotine and other mixed agonists/antagonists by the relatively low level of residual inhibition (or desensitization) that occurs after receptor activation (Papke et al., *J. Neurochem.* [2000] 75(1):204–216). Although metanicotine is particularly useful in the methods and compositions of the present invention for its ability to reduce the inhibitory effects of nAChR antagonists or mixed nAChR agonists/antagonists, therapeutic effect can also be derived from the nAChR agonistic activity exhibited by metanicotine itself.

Mixed nAChR agonists/antagonists that can be utilized in the subject invention include, but are not limited to, acetylcholine (ACh), nicotine, GTS-21 (also known as 3-[2,4-dimethoxybenzylidene]-anabaseine and DMXB), ABT-089 (also known as 2-methyl-3-(2-(S)-pyrrolidinyl methoxy) pyridine), ABT-418 (also known as (S)-3-methyl-S-(1-methyl-2-pyrrolidinyl)isoxazole), ABT-594 (also known as (R)-5-(2-azetidinyl-methoxy)-2-chloropyridine), SIB-1508Y (also known as altinicline), SIB-1553A (also known as $(\pm)$-4-{[2-(1-methyl-2-pyrrolidinyl)ethyl]thio}phenol hydrochloride), and epibatadine, or pharmaceutically acceptable salts or analogues thereof having a mixed agonist/antagonist nAChR profile. Those nAChR antagonists that can be utilized in the subject invention include, but are not limited to, mecamylamine.

The fact that metanicotine can protect nicotinic receptors from the inhibitory after-effects of other potentially therapeutic agonists is of great clinical significance. The subject invention permits the tuning of the selectivity of specific compounds to increase desired effects and diminish side effects. In this way, co-administration of metanicotine with other compounds can provide a means to tune a spectrum of effects to enhance receptor subtype-selective activation, thereby producing a more positive profile of effects. In one embodiment, metanicotine and/or the mixed nAChR agonist/antagonist interact with one or more of the nAChR $\alpha 2$–$\alpha 10$ and $\beta 2$–$\beta 4$ subunits. In another embodiment, metanicotine and/or the mixed nAChR agonist/antagonist interact with heteromeric nAChR subunit combinations of $\alpha 2$–$\alpha 6$ and $\beta 2$–$\beta 4$, homomeric nAChR subunit combinations of $\alpha 7$–$\alpha 10$, or both. In a further embodiment, metanicotine and/or the nAChR antagonist interact with one or more of the nAChR $\alpha 2$–$\alpha 10$ and $\beta 2$–$\beta 4$ subunits.

BRIEF DESCRIPTION OF THE DRAWINGS

FIG. 2A shows the concentration-response relationship for the activation of the peak currents by nicotine. Data are expressed relative to ACh maximum responses, see methods. FIG. 2B shows the concentration-response relationship for the recovery of control ACh response amplitude, measured five minutes after nicotine was applied at the indicated concentrations. Each point represents the average normalized response of at least four cells.

FIGS. 3A–3D show the concentration-response curves for the effect of DMXB and TC-2403 on $\alpha 3\beta 4$ and $\alpha 3\beta 4$ (6'F10'T) receptors. FIG. 3A shows the concentration-response relationship for the activation of the peak currents by DMXB. Data are expressed relative to Ach maximum responses, see methods. FIG. 3B shows the concentration-response relationship for the recovery of control Ach response amplitude, measured 5 minutes after DMXB was applied at the indicated concentrations. FIG. 3C shows the concentration-response relationship for the activation of the peak currents by TC-2403. Data are expressed relative to Ach maximum responses, see methods. FIG. 3D shows the concentration-response relationship for the recovery of control ACh response amplitude, measured five minutes after TC-2403 was applied at the indicated concentrations. Each point represents the average normalized response of at least four cells.

FIG. 4A shows oocytes expressing wild-type α3β4 receptors which were treated with 100 μM DMXB at a holding potential of either −50 or −100 mV. After a five minute wash at the test potential, control applications of ACh were measured and expressed relative to initial control responses obtained at the same potential. FIG. 4B shows oocytes expressing α3β4(6'F10'T) receptors which were treated with the indicated agonists at a holding potential of either −50 or −100 mV. After a five minute wash at the test potential, control applications of ACh were measured and expressed relative to initial control responses obtained at the same potential. For this experiment, the initial ACh control measurements were obtained ten minutes before the experimental agonist application in order to minimize the residual inhibition produced by the first ACh control. (* indicates p<0.05;  indicates p<0.01; * indicates p<0.001.

FIG. 5A shows raw data obtained from an oocyte expressing wild-type α3β4 receptors. The cell was first stimulated with 100 μM ACh alone (left arrow) and then with 30 DMXB in combination with 100 μM ACh (thick gray trace). After a five minute wash, the cell was re-tested with 100 μM ACh (recovery, right arrow). FIG. 5B shows data obtained from oocytes expressing wild-type α3β4 receptors treated with 30 or 100 μM DMXB, alone or in combination with 100 μM ACh. After a five minute wash, the cells were then re-evaluated for their response to control applications of 100 μM Ach. The data plotted represent average residual ACh control responses of at least four oocytes. FIG. 5C shows raw data obtained from an oocyte expressing wild-type α3β4(6'F10'T) receptors. The cell was first stimulated with 100 μM ACh alone (left arrow) and then with 30 DMXB in combination with 100 μM ACh (thick gray trace). After a five minute wash, the cell was re-tested with 100 μM Ach (recovery, right arrow). FIG. 5D shows data obtained from oocytes expressing α3β4(6'F10'T) receptors treated with 30 μM DMXB, alone or in combination with 100 μM ACh. After a five minute wash, the cells were then re-evaluated for their response to control applications of 100 μM ACh. The data plotted represent average residual ACh control responses of at least four oocytes.

FIG. 6A shows oocytes expressing wild-type α3β4 receptors which were treated with 100 μM DMXB alone or in the presence of 20 μM QX-314, 100 μM tetracaine, or TC-2403. Control 100 μM ACh responses were then measured after a five minute wash and compared to the initial ACh control responses. Only the co-application of 100 μM TC-2403 was effective at decreasing the residual inhibition measured after the application of 100 μM DMXB. In FIG. 6B, the bars on the right illustrate the results obtained when oocytes expressing L3 P4(6'F10'T) receptors were treated with 100 μM DMXB alone or in co-application with 200 μM QX-314, 100 μM tetracaine, or 100 μM TC-2403. Control 100 μM ACh responses were measured after a five minute wash and compared to the initial ACh control responses. Only the co-application of 100 μM TC-2403 was effective at decreas-ing the residual inhibition measured after the application of 100 μM DMXB. The bars on the left illustrate the results obtained when oocytes expressing α3β4(6'F10'T) receptors were treated with 300 μM nicotine alone or in co-application with 200 μM QX-314, 300 μM tetracaine, or 100 μM TC-2403. Note that nicotine is an efficacious agonist for the mutant receptor, and we have shown that the inhibitory effects of tetracaine on the mutant receptor are decreased with high levels of agonist activation (Papke, R. L. et al, Mol. Pharm. [2001] 60:1–10). Therefore, a somewhat higher concentration of tetracaine was used in this nicotine protection experiment. Control 100 μM ACh responses were measured after a five minute wash and compared to the initial ACh control responses. Only the co-application of 100 M TC-2403 was effective at decreasing the residual inhibition measured after the application of 300 μM nicotine Note that for both panels A and B, cells were pre-equilibrated for 12 seconds with QX-314, tetracaine, or TC-2403 before co-application of DMXB or nicotine with the indicated agents.

BRIEF DESCRIPTION OF SEQUENCES

Figure 1A:
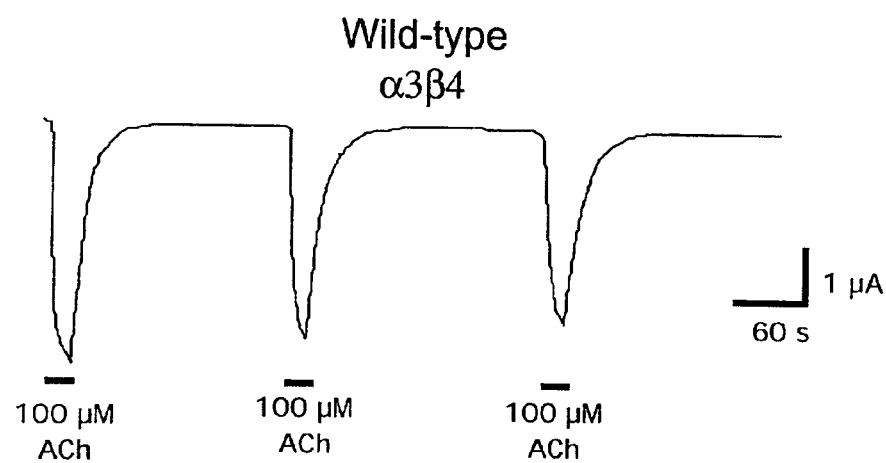
FIGS. 1A and 1B show the effects of $\beta 4$ TM2 6' 10' mutations on control ACh responses. Figure A shows control ACh responses from an oocyte expressing wild-type $\alpha 3\beta 4$ receptors showing the stability of the responses recorded at 5 minute intervals. FIG. B shows responses of oocytes expressing $\alpha 3\beta 4$ ($\beta 4$ TM2 6' 10') receptors. As shown in the upper trace, when ACh is applied at five minute intervals there is a significant drop in the second response, and then control ACh responses remain relatively stable. The lower trace shows that control ACh responses show essentially full recovery between the first and second applications with a 10 minute wash period.

SEQ ID NO. 1 is the twenty amino acid residues of the second transmembrane sequence of the nicotinic acetylcholine receptor subunit.

SEQ ID NO. 2 is the twenty amino acid residues of the second transmembrane sequence of the nicotinic acetylcholine receptor β4 subunit.

SEQ ID NO. 3 is the twenty amino acid residues of the second transmembrane sequence of the nicotinic acetylcholine receptor β1 subunit.

DETAILED DISCLOSURE OF THE INVENTION

The present invention relates to methods for the prevention or treatment of disorders, such as central nervous system disorders, which are characterized by the dysfunction of nicotinic acetylcholine receptors (nAChRs). In a preferred embodiment, the methods of the present invention involve co-administration of metanicotine, or a pharmaceutically acceptable salt or analogue thereof, and at least one compound having a mixed agonist/antagonist profile of action toward one or more nAChR subtypes to a patient. The metanicotine and the mixed nAChR agonist/antagonist can be simultaneously administered or consecutively administered. If administered simultaneously, the metanicotine and the mixed nAChR agonist/antagonist can be administered as separate compounds, or administered together as a pharmaceutical composition. Therefore, in another aspect, the present invention includes a pharmaceutical composition containing metanicotine, or a pharmaceutically acceptable salt or analogue thereof, and at least one compound having a mixed agonist/antagonist profile of action toward one or more nAChR subtypes.

As used herein, the term "agonist" means those agents or compounds that directly or indirectly interact with one or more subtypes of nAChR and stimulate or facilitate activity of the nAChR. These include both "direct agonists", i.e., those that bind to the same site on the receptor as the natural ligand, acetycholine, and "indirect agonists", i.e., those that bind to alternative sites on the receptor. Agonist activity can include stabilizing the receptor open-state, for example. As used herein, the term "antagonist" means those agents or compounds that directly or indirectly interact with one or more types of nAChR and inhibit the activity of the nAChR. Nicotinic antagonists may block the acetylcholine binding site, affect the agonist affinity state of the receptor, may block the integral ion channel itself, or they may bind to alternatives and so induce or stabilize nonconducting states of the receptor.

As used herein, the term "mixed agonist/antagonist" and "compounds exhibiting a mixed agonist/antagonist nAChR profile" refer to compounds that act as both agonists and antagonists toward at least one nAChR subtype. The agonist and antagonist activity can occur at the same nAChR subunit or at different nAChR subunits. Mixed agonists/antagonists include those compounds which, upon exposure to an nAChR, initially increase receptor activation, but will subsequently decrease receptor responsiveness ("agonist-induced residual inhibition"). Agonist-induced residual inhibition includes classical desensitization produced by the binding of agonist to the activation sites, or alternatively decrease in subsequent evoked responses due to the effect of agonist binding at sites other than those sites which promote activation. These compounds may simply be described as "agonists" or "partial agonists" in the scientific literature, and as "inhibitory agonists" herein.

Mixed nAChR agonists/antagonists that can be utilized in the subject invention include, but are not limited to, acetylcholine (ACh), nicotine, GTS-21 (also known as 3-[2,4-dimetboxybenzylidene]-anabaseine and DMXB), ABT-089 (also known as 2-methyl-3-(2-(S)-pyrrolidinyl methoxy) pyridine), ABT-418 (also known as (S)-3-methyl-S-(1-methyl-2-pyrrolidinyl)isoxazole), ABT-594 (also known as (R)-5-(2-azetidinyl-methoxy)-2-chloropyridine), SIB-1508Y (also known as altinicline), SIB-1553A (also known as (±)-4-{[2-(1-methyl-2-pyrrolidinyl)ethyl]thio}phenol hydrochloride), and epibatadine, or pharmaceutically acceptable salts or analogues thereof having a mixed agonist/antagonist nAChR profile. nAChR antagonistis that can be utilized in the subject invention include, but are not limited to, mecamylamine (also known as 3-methylamino-2,2,3-trimethylnorcamphane). Mecamylamine and other nAChR antagonists that can be utilized in the subject invention are described in U.S. Pat. No. 6,034,079 (Sanberg et al.), for example.

Receptor specificities for the above mixed nAChR agonists/antagonists have been described in the scientific literature (e.g., Papke R. L. et al., *J. Neurochem.* [2000] 75:204–216; de Fiebre et al., *Mol. Pharmacol.* [1995] 47:164–171; Meyer et al., *Brain Res.* [1997] 768:49–56; Sullivan et al., *J. Pharm. Exp. Ther.* [1997] 283:235–246; Papke et al., *Br. J. Pharm.* [1997] 120:429–438; Donnelly-Roberts et al., *J. Pharmacol. Exp. Ther.* [1998] 285:777–786; Cosford et al., *J Med Chem* [1996] 39:3235–3237; Cosford et al., *Pharm Acta Helv* [2000] 74:125–130; Washburn et al., 27th Annual Meeting of the Society for Neuroscience [1997] p. 477; Vernier et al., *J Med Chem* [1999] 42:1684–1686).

In one embodiment, metanicotine and/or the mixed nAChR agonist/antagonist interact with one or more of the nAChR α2–α9 and β2–β4 subunits. In another embodiment, metanicotine and/or the mixed nAChR agonist/antagonist interact with heteromeric nAChR subunit combinations of α2–α6 and β2–β4, homomeric nAChR subunit combinations of α7–α9, or both. In a further embodiment, metanicotine and/or the nAChR antagonist interact with one or more of the nAChR α2–α10 and β2–β4 subunits.

Neurological disorders that can be treated with the methods and compositions of the subject invention include disorders associated with dysfunction of nAChRs activity and particularly those disorders characterized by dysfunction of nicotinic cholinergic neurotransmission, including disorders involving neuromodulation of neurotransmitter release. The nAChR dysfunction can involve hyperactivity or hypoactivity of one or more nAChR subtypes. nAChR hypoactivity can be caused, for example, by dysfunction of existing receptors, or by deficits of binding sites related to alterations of nAChR synthesis on the levels of (i) transcription, (ii) translation and posttranslational modifications, and (iii) receptor transport and turnover, including membrane insertion.

The methods and pharmaceutical compositions of the present invention are useful for treating those types of conditions and disorders for which other types of nicotinic receptor ligands have been proposed as therapeutics, for example. The methods and pharmaceutical compositions of the present invention are useful for the prevention and treatment of disorders, such as central nervous system (CNS) disorders, that are characterized by an alteration in normal nAChR function, e.g., alteration in normal neurotransmitter release. Such neurological disorders can be drug induced; can be attributed to genetic predisposition, infection or trauma; or can be of unknown etiology. Such neurological disorders include neuropsychiatric disorders, neurological diseases and mental illnesses; and include neurodegenerative diseases, behavioral disorders, cognitive disorders and cognitive affective disorders.

Preferably, the methods and compositions of the subject invention are administered to treat a patient suffering from a neurological disorder associated with dysfunction of one or more subtypes of neuronal nAChR. Neurological disorders which can be treated with pharmaceutical compositions of the present invention, and in accordance with methods of the present invention, include, but are not limited to, presenile dementia (early onset Alzheimer's disease), senile dementia (dementia of the Alzheimer's type), Parkinsonism including Parkinson's disease, Huntington's chorea, tardive dyskinesia, hyperkinesias, mania, attention deficit disorder, attention deficit hyperactivity disorder, sleep-wake disorders, chronic-fatigue syndrome, tremor, epilepsy, neuropathic pain, addiction (e.g., nicotine addiction), anxiety, dyslexia, schizophrenia, obsessive-compulsive disorder, and Tourette's syndrome.

Other disorders associated with dysfunction of one or more subtypes of neuronal nAChR which can be treated with the pharmaceutical compositions of the present invention, and in accordance with methods of the present invention, can be found throughout the scientific literature (e.g., Benowitz N. L., *Annu. Rev. Pharmacol. Toxicol.* [1996] 36:597–613; Vidal C., *Mol. Chem. Neuropathol.* [1996] 28:3–11; Newhouse P. A. et al., *Drugs Aging* [1997] 11:206–228; Adler L. E. et al., *Schizophr. Bull.* [1998] 24:189–202; Lloyd G. K. et al., *Life Sci.* [1998] 62:1601–1606; Lloyd G. K. and Williams M., *Brain Res.* [2000] 768:49–56; Mihailescu S. and Drucker-Colin R., *Arch. Med. Res.* [2000] 31:131–144; Newhouse P. A. and Kelton M., *Pharm. Acta. Helv.* [2000] 74:91–101; Rusted J. M., and Newhouse P. A., *Behav. Brain Res.* [2000] 113:121–129; and Young J. M. et al. *Clin. Ther.* [2001] 23:532–565).

The methods and pharmaceutical compositions of the present invention provide therapeutic benefit to individuals suffering from such disorders and exhibiting clinical manifestations of such disorders in that the compounds within those compositions, particularly when employed in effective amounts, have the potential to (i) exhibit nicotinic pharmacology and affect relevant nicotinic receptor sites (e.g., act as a pharmacological agonist to activate nicotinic receptors), and (ii) elicit neurotransmitter secretion, and hence prevent and suppress the symptoms associated with those diseases. In addition, the compounds have the potential to (i) increase the number of nicotinic cholinergic receptors of the brain of the patient, (ii) exhibit neuroprotective effects, and/or (iii) when employed in effective amounts do not cause appreciable adverse side effects (e.g., significant increases in blood pressure and heart rate, significant negative effects upon the gastro-intestinal tract, and significant effects upon skeletal muscle).

The present invention also relates to a method for providing prevention of a neurological condition or disorder to a patient susceptible to such a condition or disorder. For example, the method involves administering to a patient an amount of metanicotine and an amount of a compound having either antagonist nAChR activity, or mixed agonist/antagonist nAChR activity, wherein the metanicotine and compound are, together, effective for providing some degree of prevention of the progression of a neurological disorder (i.e., provide protective effects), amelioration of the symptoms of a neurological disorder, and amelioration of the reoccurrence of a neurological disorder. The methods of the present invention also involve administering an effective amount of a pharmaceutical composition incorporating a compound having either an nAChR antagonist activity profile or a mixed agonist/antagonist nAChR activity profile, and metanicotine, or a pharmaceutically acceptable salt or analogue thereof. Alternatively, the method involves the co-administration of a compound having an antagonist nAChR activity profile or a mixed agonist/antagonist nAChR activity profile, and metanicotine, where the compound is administered consecutively (before or after), or simultaneous with, metanicotine. The compounds can optionally be optically active, possessing substituent groups of a character such that those compounds possess optical activity. Optically active compounds can be employed as racemic mixtures or as enantiomers.

As some of the compounds exhibiting antagonist nAChR profiles or mixed agonist/antagonist nAChR profiles exhibit analgesic effects, the methods of the subject invention also pertain to methods for alleviating pain in a patient by co-administering metanicotine and a compound exhibiting either antagonist activity, or both agonist and antagonist activity, toward one or more nAChRs, wherein the compound also exhibits analgesic activity. The inhibitory effects of the compound on the activity of one or more nAChR subtypes is reduced by co-administration of metanicotine, thereby reducing any side-effects associated with the inhibition, and increasing the compound's therapeutic effectiveness.

The manner in which metanicotine and the nAChR antagonist, or metanicotine and the mixed nAChR agonist/antagonist, can be administered can vary. The compounds and compositions can be administered by inhalation; in the form of an aerosol either nasally or using delivery articles of the type set forth in U.S. Pat. No. 4,922,901 to Brooks, et al and U.S. Pat. No. 5,099,861 to Clearman et al; orally (e.g., in liquid form within a solvent such as an aqueous liquid, or within a solid carrier); intravenously (e.g., within a saline solution); or transdermally (e.g., using a transdermal patch). Exemplary methods for administering such compounds and compositions will be apparent to the skilled artisan. Certain methods suitable for administering compounds and compositions useful according to the subject invention are set forth in U.S. Pat. No. 4,965,074, to Leerson. The administration can be intermittent, or at a gradual, continuous, constant or controlled rate.

The compounds used in the subject invention, including metanicotine, the nAChR antagonist, and the mixed nAChR agonists/antagonists, can each be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, tritheylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

As used herein, "analogues" of metanicotine include those compounds which reduce or eliminate one or more of the inhibitory effects of a nAChR antagonist or a mixed nAChR agonist/antagonist, when the metanicotine analogue is co-administered with the nAChR antagonist or the mixed nAChR agonist/antagonist. As used herein, "analogues" of a particular nAChR antagonist include those compounds which retain the ability to have an antagonistic effect on one or more subtypes of nAChR and "analogues" of a particular mixed nAChR agonist/antagonist include those compounds which retain the ability to have both an agonistic effect and antagonistic effect on one or more subtypes of nAChR.

The patient being administered the metanicotine and nAChR antagonist, or metanicotine and mixed nAChR agonist/antagonist, can be a human being, or other mammal.

The dose of metanicotine and nAChR antagonist, or metanicotine and mixed nAChR agonist/antagonist, is that amount effective to treat the neurological condition from which the patient suffers or is susceptible to. As used herein, the terms "effective amount", "effective dose", or "therapeutic amount" are intended to mean that amount sufficient to pass across the blood-brain barrier of the patient, to interact with relevant receptor sites in the brain of the patient, and to elicit neuropharmacological effects (e.g., elicit neurotransmitter secretion, thus resulting in effective treatment of the disease or condition). The effective dose can vary, depending upon factors such as the condition of the patient, the severity of the symptoms of the disorder, and the manner in which the metanicotine and mixed nAChR agonist/antagonist is administered. Treatment of a neurological condition involves a decrease of one or more symptoms associated with the palticular condition.

The metanicotine and nAChR antagonist, or metanicotine and mixed nAChR agonist/antagonist, administered according to the methods of the subject invention can traverse the blood-brain barrier of the patient. As such, they have the ability to enter the patient's central nervous system. The log P values of typical compositions, which are useful in carrying out the present invention are generally greater than about −0.5, often are greater than about 0, and frequently are greater than about 0.5. The log P values of such compositions are generally less than about 3, often are less than about 2, and frequently are less than about 1. Log P values provide a measure of the ability of a compound to pass across a diffusion barrier, such as a biological membrane. See, for example, Hansch, et al., *J. Med. Chem.* 11:1 (1968).

The pharmaceutical compositions of the subject invention have the ability to modulate one or more nAChR functions, such as secretion of a neurotransmitter or upregulation of one or more types of nAChR. The compositions of the subject invention have the ability to bind to, and cause activation of, nicotinic cholinergic receptors of the brain of the patient. As such, such compositions have the ability to act as nicotinic agonists. nAChR function that may be modulated includes neurotransmitter release, such as acetylcholine, dopamine, serotonin, and norepinephrine, from the relevant neurons (Summers and Giacobini, *J. Neurosci. Res.* [1995] 20:683–689; Summers et al., *Neurochem. Res.* [1996] 21:1181–1186).

The metanicotine and nAChR antagonist, or metanicotine and mixed nAChR agonist/antagonist, whether administered

Materials and Methods cDNA clones. Rat cDNA clones for the neuronal receptors (Heinemann et al., *Proceedings of NATO Conference on Mechanism of Action of Nicotinic Acetylcholine Receptor* [1986]) were used. The sequences of the TM2 domains of the relevant subunits are shown below. Adopting the terminology proposed by Miller et al. (Miller, C. *Neuron* [1988] 2:1195–1205), the 20 residues in the proposed second transmembrane sequence are identified as 1' through 20'.

```
          intracellular    MEMBRANE SPANNING II           extracellular
ALPHA3   ValThrLeuCysIleSerValLeuLeuSerLeuThrValPheLeuLeuValIleThrGluThrIleProSerThr    (SEQ ID NO. 1)

BETA4    MetThrLeuCysIleSerValLeuLeuAlaLeuThrPhePheLeuLeuLeuIleSerLysIleValProProThr    (SEQ ID NO. 2)

BETA1    MetGlyLeuSerIlePheAlaLeuLeuThrLeuThrValPheLeuLeuLeuLeuAlaAspLysValProGluThr    (SEQ ID NO. 3)
         1'              6'        10'                              20'
``` separately, or as a pharmaceutical composition of the present invention, can include various other components as additives or adjuncts. Exemplary acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anesthetics, steroids, and corticosteroids. Such components can provide additional therapeutic benefit, act to affect the therapeutic action of the metanicotine and mixed nAChR agonist/antagonist, or act towards preventing any potential side effects which may be posed as a result of administration of the metanicotine and mixed nAChR agonist/antagonist.

The metanicotine and nAChR antagonist, or metanicotine and mixed nAChR agonist/antagonist, whether administered separately or as a pharmaceutical composition of the subject invention, can be formulated according to known methods for preparing pharmaceutically useful compositions. Formulations are described in a number of sources which are well known and readily available to those skilled in the art. For example, *Remington's Pharmaceutical Science* (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

All patents, patent applications, and publications referred to or cited herein are incorporated by reference in their entirety to the extent they are not inconsistent with the explicit teachings of this specification.

Construction of site-directed mutants. Site-directed mutagenesis was conducted with QUICKCHANGE kits (STRATAGENE, LaJolla, Calif.). In brief, two complimentary oligonucleotides were synthesized which contain the desired mutation flanked by 10–15 bases of unmodified nucleotide sequence. Using a thermal cycler, Pfu DNA polymerase extended the sequence around the whole vector, generating a plasmid with staggered nicks. Each cycle built only off the parent strands, therefore there was no amplification of misincorporations. After 12–16 cycles, the product was treated with Dpn I, which digested the methylated parent DNA into numerous small pieces. The product was then transformed into *E. coli* cells, which repaired the nicks. Mutations were confirmed by DNA sequencing.

Preparation of RNA. After linearization and purification of cloned cDNAs, RNA transcripts were prepared in vitro using the appropriate mMessage mMachine kit from AMBION Inc. (Austin, Tex.).

Expression in Xenopus oocytes. Mature (>9 cm) female *Xenopus laevis* African toads (NASCO, Ft. Atkinson, Wis.) were used as a source of oocytes. Prior to surgery, frogs were anesthetized by placing the animal in a 1.5 g/L solution of MS222 (3-aminobenzoic acid ethyl ester). Eggs were removed from an incision made in the abdomen. In order to remove the follicular cell layer, harvested oocytes were treated with collagenase (1.25 mg/ml) from Worthington Biochemical Corporation (Freehold, N.J.) for 2 hours at room temperature in calcium-free Barth's solution (88 mM NaCl, 10 mM HEPES pH 7.6, 0.33 mM MgSO$_4$, 0.1 mg/ml gentamicin sulfate). Subsequently, stage 5 oocytes were isolated and injected with 50 nl (5–20 ng) each of a mixture of the appropriate subunit cRNAs following harvest. Recordings were made 1 to 7 days after injection depending on the cRNAs being tested.

Chemicals. DMXB (GTS-21) was supplied by Taiho Pharmaceuticals (Japan). QX-314, tetracaine, (−)-Nicotine, and all other chemicals for electrophysiology were obtained from Sigma Chemical Co. (St. Louis Mo.). Fresh acetylcholine stock solutions were made daily in Ringer's solution and diluted.

Electrophysiology. Oocyte recordings were made with a Warner Instruments (Hamden, Conn.) OC-725C oocyte amplifier and RC-8 recording chamber interfaced to either a Macintosh or Gateway personal computer. Data were acquired using Labview software (NATIONAL INSTRUMENTS) or pClamp8 (AXON INSTRUMENTS) and filtered at a rate of 6 Hz. Oocytes were placed in a Warner recording chamber with a total volume of about 0.6 ml and perfused at room temperature with frog Ringer's solution (115 mM NaCl, 2.5 mM KCl, 10 mM HEPES pH 7.3, 1.8 mM CaCl$_2$) containing 1 μM atropine to inhibit potential muscarinic responses. A Mariotte flask filled with Ringer's solution was used to maintain a constant hydrostatic pressure for drug deliveries and washes. Drugs were diluted in perfusion solution and loaded into a 2 ml loop at the terminus of the perfusion line. A bypass of the drug-loading loop allowed bath solution to flow continuously while the drug loop was loaded, and then drug application was synchronized with data acquisition by using a 2-way electronic valve. The rate of bath solution exchange and all drug applications was 6 ml/min. Current electrodes were filled with a solution containing 250 mM CsCl, 250 mM CsF and 100 mM EGTA and had resistances of 0.5–2 MΩ. Voltage electrodes were filled with 3 M KCl and had resistances of 1–3 MΩ.

Experimental protocols and data analysis. Current responses to drug application were studied under two-electrode voltage clamp at a holding potential of −50 mV unless otherwise noted. Holding currents immediately prior to agonist application were subtracted from measurements of the peak response to agonist. All ACh and other drug applications were separated by wash periods of 5 minutes unless otherwise noted. At the start of recording, all oocytes received two initial control applications of 100 μM ACh. While there was frequently a rundown between the first and second responses to 100 μM ACh, it was determined in a series of control experiments, that for both the wild-type and mutant receptors, ACh responses were essentially stable after the second 100 μM ACh application (see FIG. 1). Once ACh responses stabilized, responses to experimental drug applications were obtained in alternation with further 100 μM control ACh applications. In order to correct for the variability in the level of channel expression in each oocyte, all drug application responses were normalized to the respective ACh control response obtained 5 minutes previous to the experimental drug application.

In order to measure residual inhibitory effects of experimental drug applications, and to otherwise confirm the continued stability of the ACh control responses in a given cell, comparisons were made between the responses to 100 μM ACh obtained 5 minutes before an experimental drug application (C1) and the 100 μM ACh response obtained after a further 5 minute wash (C2). The ratio of C2/C1 is referred to as the recovery response (FIGS. 2B, 3B and 3D). Measurements of C2/C1 that were <0.75 were taken to indicate that the experimental drug application produced some form of residual inhibition. An oocyte was not used for further experimental drug applications when the measurements of C2/C1 became less than 0.75.

Means and standard errors (SEM) were calculated from the normalized responses of at least four oocytes for each experimental concentration. For concentration-response relations (FIGS. 2 & 3), data were plotted using Kaleidagraph 3.0.2 (ABELBECK SOFTWARE; Reading, Pa.), and curves were generated from the Hill equation.

$$\text{Response} = \frac{I_{max}[agonist]^n}{[agonist]^n + (EC50)^n} \quad \text{(Formula I)}$$

In Formula I, $I_{max}$ denotes the maximal response for a particular agonist/subunit combination, and n represents the Hill coefficient. $I_{max}$, n, and the EC50 were all unconstrained for the fitting procedures. In order to show the relative efficacy of each experimental agonist compared to ACh, for all the concentration response curves, the data were initially normalized to the 100 μM ACh responses obtained in the same cells and then scaled by the ratio of 100 μM ACh control responses to the maximal ACh responses determined in separate experiments (not shown). For both the wild-type and mutant receptors, maximal responses to ACh were obtained with 1 mM ACh. The responses of wild-type and mutant receptors to 1 mM ACh were respectively, 2.9±0.2 (n=4) and 1.7±0.13 (n=4) times larger than the 100 μM ACh control responses in the same cells.

As noted above, measurements of agonist-induced residual inhibition were made based on changes in the response to control 100 μM ACh applications. The values for the C2/C1 ratios were plotted as functions of the experimental agonist concentrations applied between the C2 and C1 control responses. The data were then fit to the Hill equation with n constrained to equal −1 for the calculation of IC50 values. Determination of significant differences between experimental and control groups (FIGS. 4A–4B and 5A–5D) was made by t-test (unpaired two-tailed).

For experiments assessing voltage-dependence of inhibition, oocytes were voltage-clamped at the indicated holding potential for both control applications of ACh alone and test applications of experimental agonists and/or antagonists. After a 5 minute wash period, cells were given another control ACh application at the indicated potential so that residual inhibition could be evaluated.

Following are examples which illustrate procedures for practicing the invention. These examples should not be construed as limiting. All percentages are by weight and all solvent mixture proportions are by volume unless otherwise noted.

EXAMPLE 1

Figure 1B:
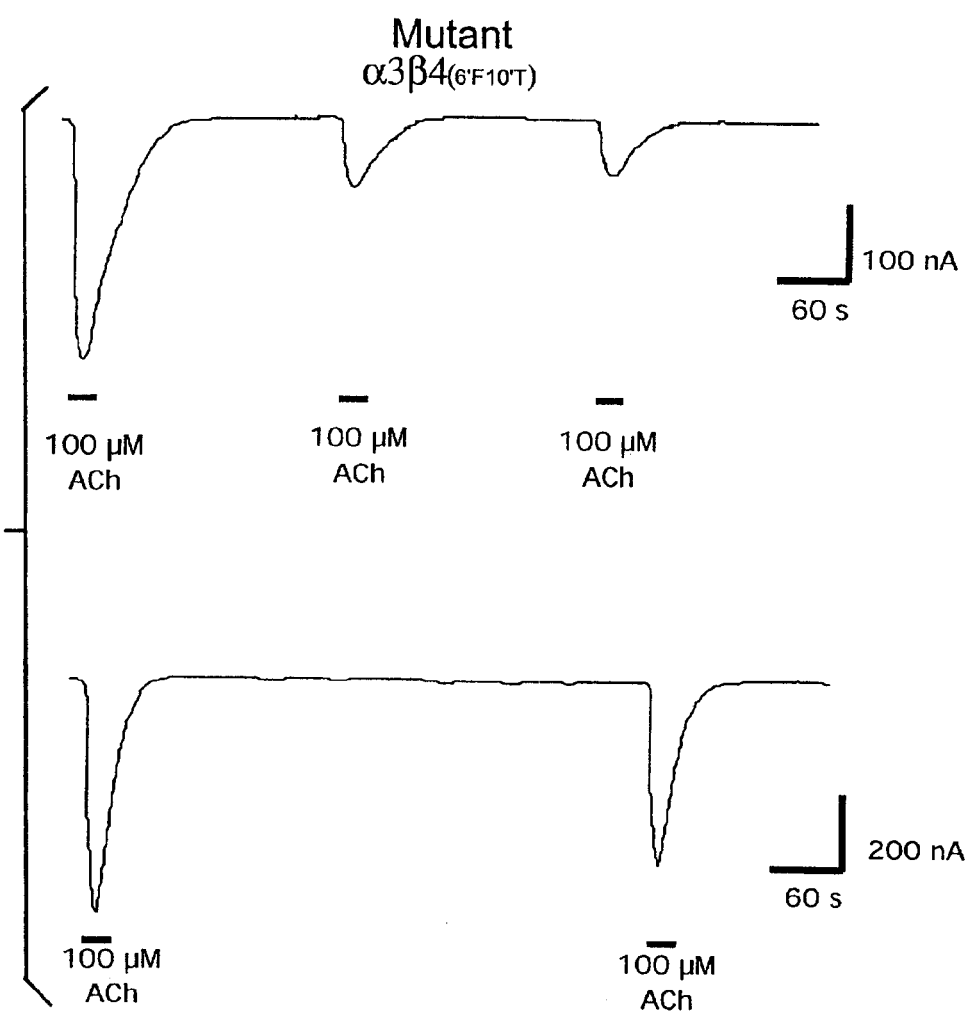

Beta Subunit TM2 Mutations Promote Agonist-Induced Residual Inhibition by ACh and Nicotine As previously reported for receptors containing chimeric β4 subunits (Webster, J. C. et al., *Br. J. of Pharmacol.* [1999] 127:1337–1348), receptors containing the β4 6' and 10' point mutations showed decreased responses to repeated applications of ACh and nicotine, suggesting that these agonists produce some form of residual inhibition, as shown in FIGS. 1A and 1B. While the inhibition produced by nicotine persisted for up to an hour (not shown), inhibition produced by ACh was more reversible, with essentially full recovery after 7–8 minutes of wash.

Figure 2A:
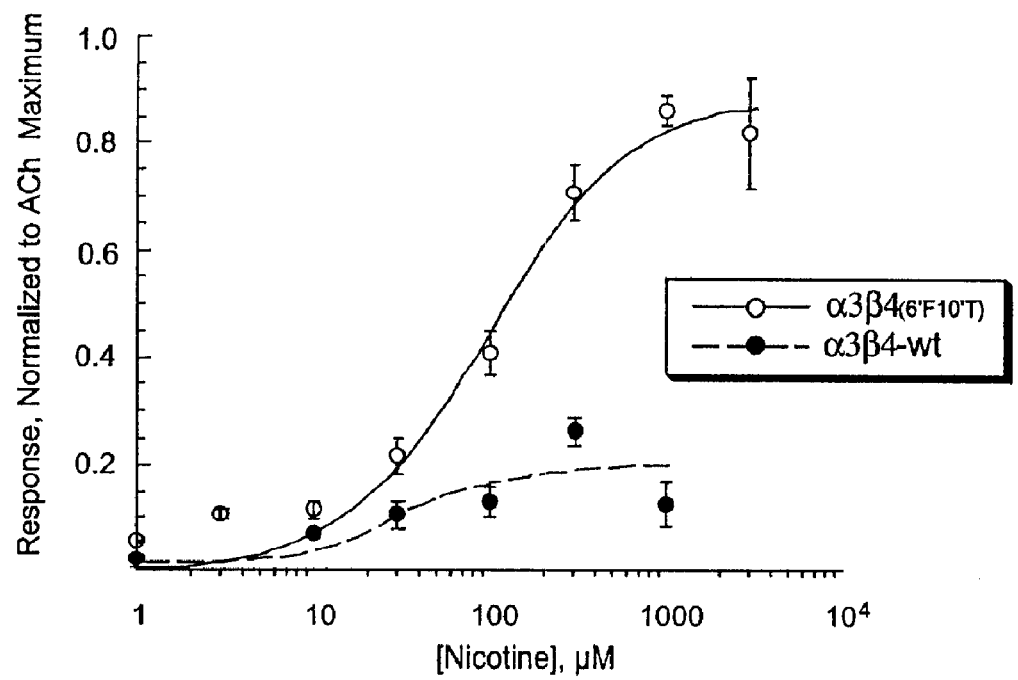
FIGS. 2A and 2B show the concentration-response curves for the effect of nicotine on $\alpha 3\beta 4$ and $\alpha 3\beta 4(6'F10'T)$ receptors.
Figure 2B:
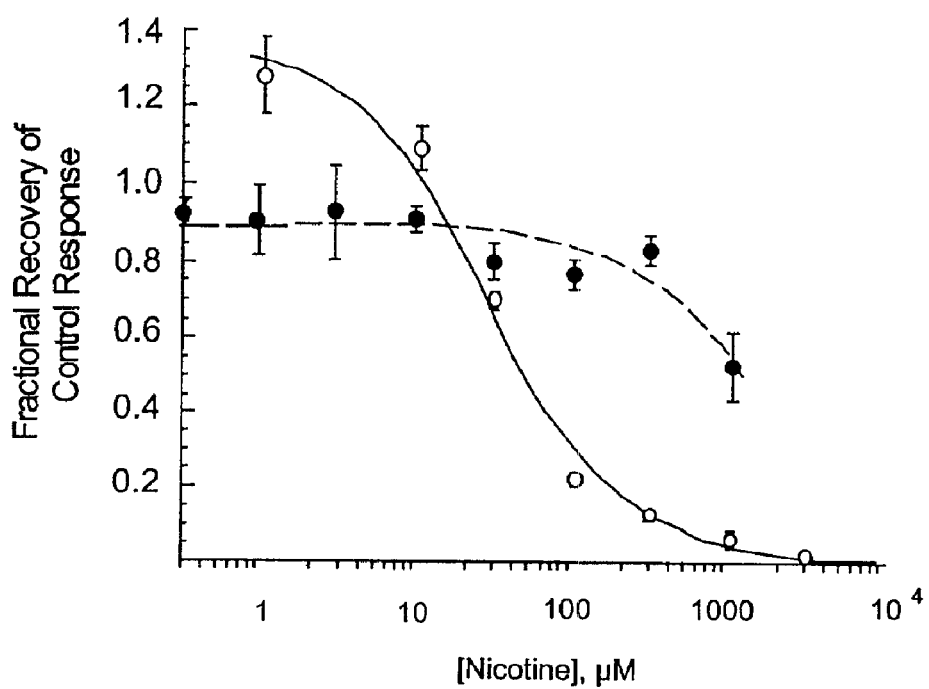

The concentration-response function for nicotine's activation and inhibition of wild-type and mutant receptors is shown in FIGS. 2A and 2B. The presence of the 6' and 10' mutations in the β4☐ subunit appeared to increase the efficacy of nicotine compared to ACh and to substantially increase the agonist-induced residual inhibition measured after a 5 minute wash. However, the interpretation of the efficacy data in FIG. 2A is complicated by the fact that the measurement is based on comparison to ACh-evoked currents. Noncompetitive inhibitory or desensitizing effects limit the apparent efficacy of nicotine in wild-type α3-containing receptors (Papke, R. L. et al, *J. Neurochem.* [2000] 75:204–216), and the effect of the 6'/10' mutations seems to be primarily on the rate of recovery from nicotine-induced inhibition. It may be the case that the 6'/10' mutations are having the effect of producing more agonist-induced residual inhibition during an ACh-evoked response. If this is the case, then much of the apparent increase in nicotine's relative efficacy may be due to a decrease in ACh's absolute efficacy.

Figure 4A:
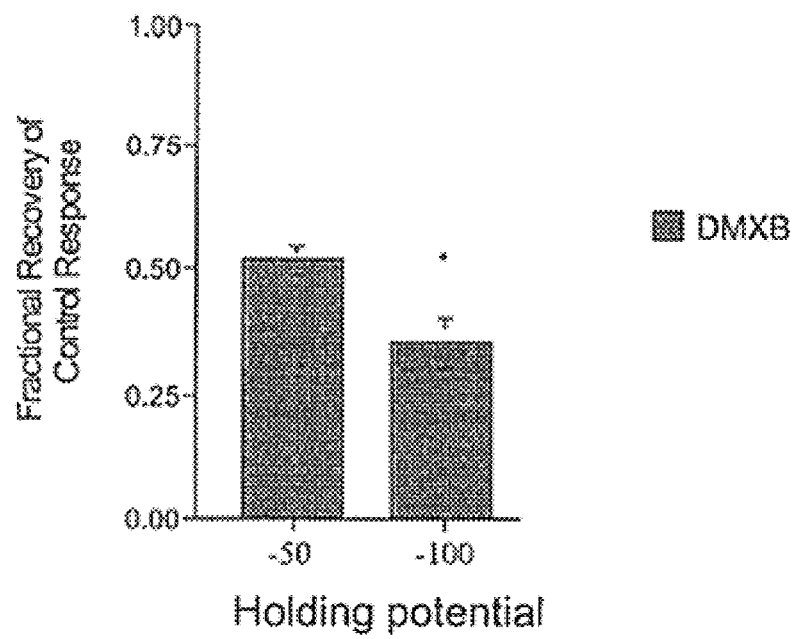
FIGS. 4A and 4B show the effect of hyperpolarization on the inhibition measured after the application of agonists.
Figure 4B:
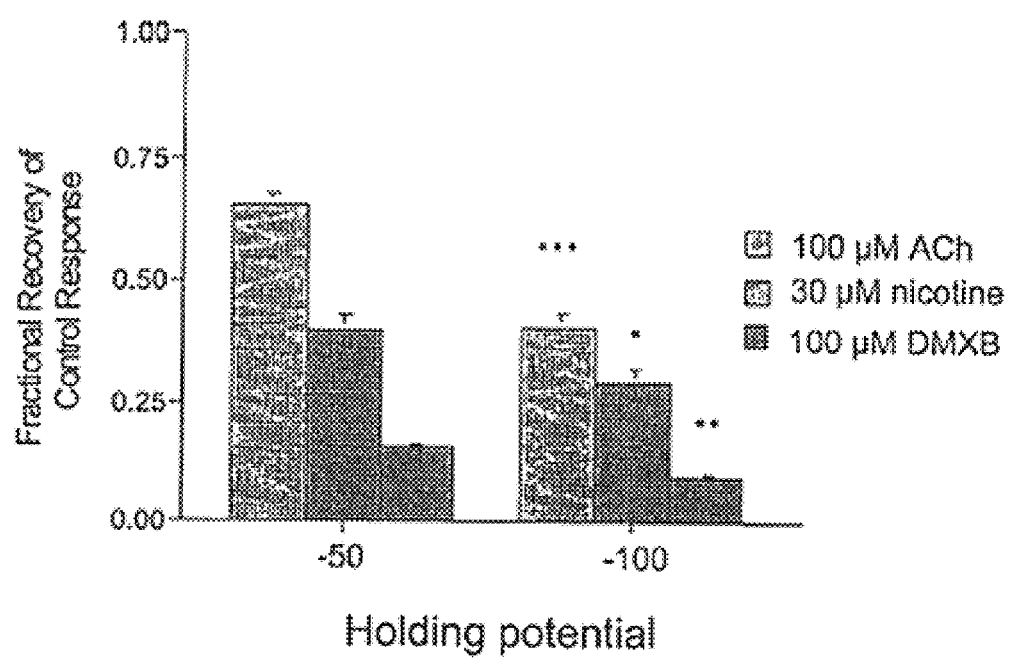

EXAMPLE 2
TM2 Mutations Differentially Regulate the Activation and Inhibition of Subtype-selective Agonists As shown in FIGS. 2A and 2B, the 6'/10' mutations appear to influence both activation and agonist-induced residual inhibition, raising the question of whether these effects are likely to represent multiple consequences of these agonists binding to a single site on the receptor (i.e. the activation binding site), or alternatively represent effects from binding to multiple sites on the receptors. In order to test this, the effects of other agonists on the wild-type and mutant receptors were investigated. Specifically, two subtype-selective agents were used that previously have been reported to be only weak partial agonists on wild-type α3β4□ receptors, DMXB and TC-2403 (metanicotine). DMXB is an α7-selective partial agonist (Meyer, E. M. et al., *Brain Res.* [1997] 768:49–56) that can produce agonist-induced residual inhibition of wild-type receptors in the absence of strong activation. As shown in FIG. 3A, the 6'/10' β4□ mutations did not cause DMXB to appear as a more efficacious agonist than for the wild-type receptor, but they did cause DMXB to produce more inhibition after it was applied at 100 or 300 μM ($p<0.001$), as shown in FIG. 3B. In contrast, the greatest effect of the 6'/10' β4 mutations on the activity of the α4β2-selective agonist TC-2403 was in measurement of apparent efficacy, as shown FIG. 3C, since there was no significant increase in residual inhibition at concentrations less than 1 mM, as shown in FIG. 3D. Even after the application of 1 mM TC-2403, residual inhibition was minimal; responses were still 70±6% of the pre-application control values.

α3β4(6'F10'T) mutant receptors by nicotine and ACh to see if the inhibition had properties that would be consistent with open channel blockade. Cells were held at either −50 mV or −100 mV and tested for their response to control concentrations of ACh. After a 10 min wash, test agonists (ACh, DMXB or nicotine) were applied at the concentrations indicated. Cells were then washed for 5 min and tested again for their response to a control ACh application. Cells were held at the indicated holding potential throughout the entire procedure. As shown in FIGS. 4A and 4B, the residual inhibition of both wild-type and mutant receptors was enhanced if the cells were held at a hyperpolarized potential. This would be consistent with inhibition associated with binding to a channel-associated site (e.g. open channel block).

EXAMPLE 4
DMXB-Induced Inhibition of Mutant Receptors is Use-Dependent

Figure 5A:
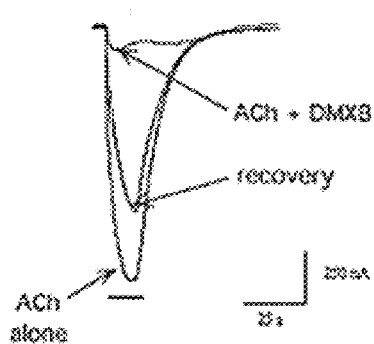
FIGS. 5A–5D show use-dependence of inhibition by DMXB.
Figure 5B:
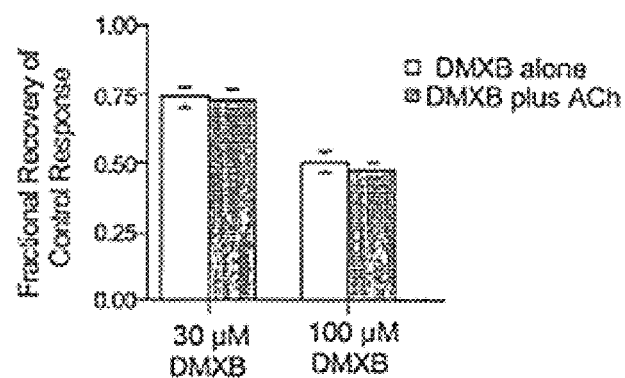
Figure 5C:
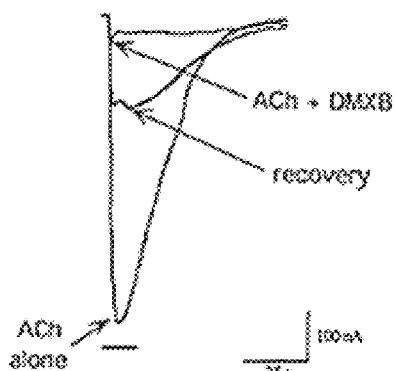
Figure 5D:
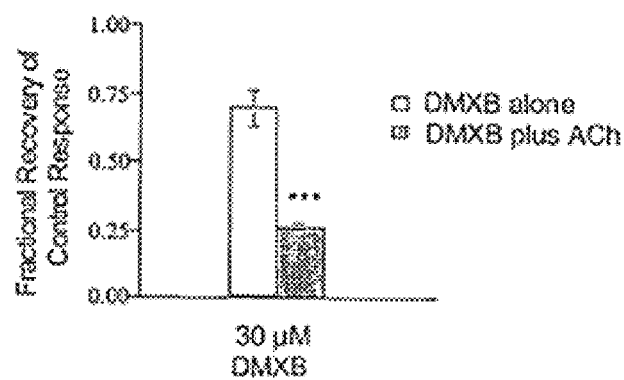

As shown in FIG. 5A, the inhibition of wild-type α3β4 receptors by DMXB is not enhanced when the weak partial agonist DMXB is co-applied with the strong agonist ACh. This is in contrast with the previous observation that DMXB-induced inhibition of α4β2 receptors is enhanced when the drug is co-applied with ACh (de Fiebre, C. M. et al. *Mol. Pharmacol.* [1995] 47:164–171). Interestingly, this property is apparently altered in the receptors containing the β4(6'F10'T) subunit, such that the co-application of ACh with 30 μM DMXB produced a large increase in the residual inhibition, as shown in FIG. 5B. While the results presented in FIGS. 5A–5D suggest a clear difference in the inhibition of wild-type and mutant receptors by DMXB, interpretation of the data should also include consideration that as a weak partial agonist, DMXB effectively prevents ACh from being

TABLE I

| | | Curve fits for Hill equations | | | |
|---|---|---|---|---|---|
| Agonist | Receptor | Max response* | n | $EC_{50}$ (μM) | FIG. reference |
| Nicotine | α3β4 | 0.88 ± 0.04 | 1.2 ± 0.2 | 96 ± 16 | 2A |
| | α3β4 (6'F10'T) | 0.20 ± 0.05 | 0.8 ± 0.3 | 30 ± 18 | 2B |
| TC-2403 | α3β4 | 0.09 ± 0.01 | 2.1 ± 0.2 | 347 ± 12 | 3C |
| | α3β4 (6'F10'T) | 0.38 ± 0.01 | 2.1 ± 0.2 | 111 ± 5 | 3C |
| ACh[†] | α3β4 | 1.0 | 2.1 ± 0.6 | 68 ± 12 | |
| | α3β4 (6'F10'T) | 1.0 | 0.8 ± 0.1 | 72 ± 17 | |

*relative to ACh Maximum
[†]data taken from Papke et al., 2001

TABLE II

| | | $IC_{50}$ values | | |
|---|---|---|---|---|
| Drug | Receptor | Holding potential | $IC_{50}$ (μM) | FIG. reference |
| Nicotine | α3β4 | −50 | >1000 | 2B |
| | α3β4 (6'F10'T) | −50 | 29 ± 5 | 2B |
| DMXB | α3β4 | −50 | 121 ± 48 | 3B |
| | α3β4 (6'F10'T) | −50 | 23 ± 17 | 3B |

EXAMPLE 3
The Residual Inhibition Produced by Agonists is Voltage Dependent

The voltage dependence of the residual inhibition of wild-type α3β4 and α3β4(6'F10'T) receptors produced by DMXB was evaluated, as well as the enhanced inhibition of effective during the co-applications. That is, since DMXB is apparently capable of both competitive interactions with ACh at the activation site, and a use-dependent binding to a channel associated site, when ACh is co-applied with DMXB, ACh cannot promote the use-dependent effects because DMXB is blocking activation. Specifically, the responses of both wild-type and mutant receptors to 100 μM ACh were decreased a similar amount when the ACh was co-applied with 30 μM DMXB. The responses of α3β4 zα3β4(6'F10'T) receptors were reduced to 13±2%. When 100 μM DMXB was co-applied to wild-type receptors with 100 μM ACh, the activation was only 4±0.2% the activation produced by ACh alone. It may be the case that, for the wild-type receptors, DMXB may have a similar affinity for both activation sites and inhibitory sites so that competitive inhibition masks use-dependent effects. If in the mutant receptors, there is increase only in affinity for the inhibitory site, compared to wild-type, then use-dependent inhibition would become more apparent.

Figure 6A:
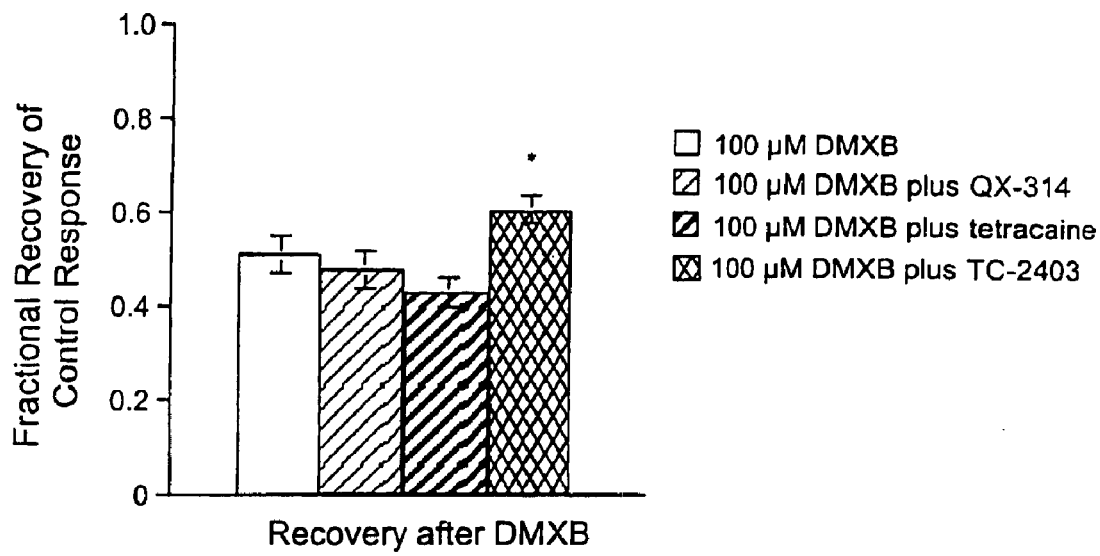
FIGS. 6A and 6B show protection of receptor function.
Figure 6B:
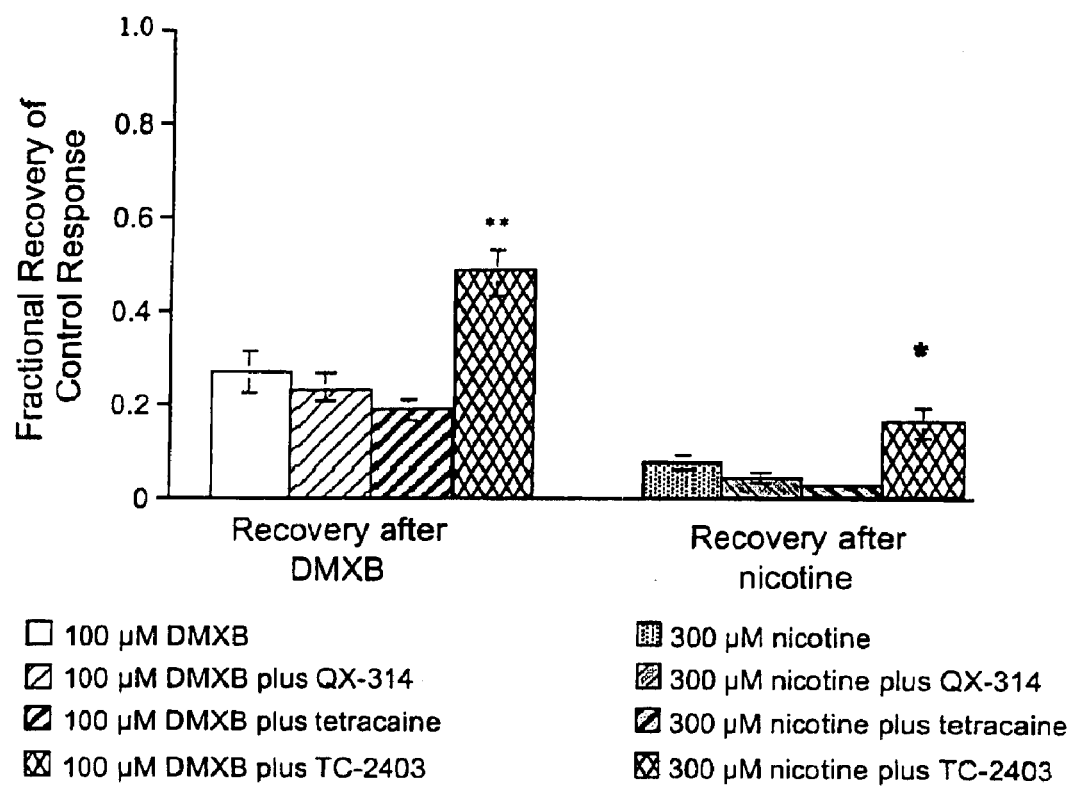

EXAMPLE 5
Protection of (6'F10'T) Receptors from Residual Inhibition Produced by Mixed Agonists/Antagonists Since QX-314 (also known as 2-(triethylamino)-N-(2,6-dimethylphenyl)-acetamide) and tetracaine both produce a readily reversible voltage-dependent inhibition of α3β4 receptors, it was determined whether, by pre-treating the receptors with a high concentration of these agents so as to saturate their binding sites, the receptors' function could be protected from the relatively long-lived inhibition produced by the application of 100 μM DMXB. As shown in FIG. 6A, neither of these agents provided any protection from the DMXB-induced inhibition. However, when cells were pre-treated with TC-2403 (metanicotine), there was a significant ($p<0.05$) reduction in the residual inhibition produced by DMXB, as shown in FIG. 6A. These same agents were evaluated for their ability to protect α3β4(6'F10'T) receptors from the residual inhibition produced by either 100 μM DMXB or 300 μM nicotine. As shown in FIG. 6B, significant protection of receptor function was provided by TC-2403 and not by the local anesthetics ($p<0.01$ for DMXB inhibition and $p<0.05$ for nicotine inhibition).

The mutations characterized in the beta subunit TM2 domain were first identified because they determined the sensitivity of neuronal receptor subtypes to selective non-competitive inhibitors classified as ganglionic blockers based on their preferential inhibition of receptors containing neuronal-type beta subunits (i.e. β2 or β4). It was noted that in addition to having a reduced sensitivity to the classic ganglionic blocker mecamylamine, compared to wild-type, receptors with the β4(6'F10'T) subunit also showed increased residual inhibition after exposure to nicotine (Webster, J. C. et al., *Br. J. of Pharm.* [1999] 127:1337–1348). Therefore, in order to determine to what extent the effects of these mutations might be generalized to other agonists, the analysis of α3β4(6'F10'T) receptors was expanded to look at the effects of these mutations on the activity of the two selective partial agonists DMXB and TC-2403. Competition experiments were conducted in order to determine whether the increased agonist-induced residual inhibition observed was most consistent with enhanced desensitization, channel block by agonist (steric inhibition), or alternatively some form of allosteric inhibition.

A strict classical definition of desensitization requires that the inhibition follows from binding to the very same sites where the agonists bind to promote channel activation. On the other hand, channel block or "steric" inhibition would be distinguished as the binding of the agonist molecules to a site (or sites) within the conduction pathway, such that the presence of the agonist prevents current flow. In the case of allosteric inhibition, the agonists would be assumed to be binding to a class of sites that selectively stabilized the closed or desensitized states without directly blocking the channel.

The results obtained with the two selective agonists DMXB and TC-2403 suggest that the effects of the 6'/10' mutations on apparent efficacy and inhibition may not be interdependent since DMXB manifested only increased inhibition and TC-2403 manifested primarily an increase in relative efficacy. One possibility might be that the mutations are affecting the coupling efficiency between agonist binding and channel gating for some agonists (i.e. nicotine and TC-2403), but at the same time improving a binding site within the channel for a steric inhibition (i.e. open-channel block) by other agonists (i.e. all but TC-2403). Alternatively, the mutations may simply promote more rapid desensitization (although, again TC-2403 would be the exception).

However, defining desensitization as an inactivation process promoted by the binding (or retention of) agonist at the activation binding site, it would seem unlikely that the inactivation of α3β4(6'F10'T) receptors by DMXB would represent desensitization since it is promoted by the binding of ACh to the activation site. This apparent use-dependence would also suggest that DMXB, nicotine, and ACh may have their enhanced inhibitory effects by binding to sites within the ion channel such as those associated with open channel block. Such a mechanism would also be consistent with the observed voltage dependence for inhibition of both the wild-type and mutant receptors.

The local anesthetic QX-314 has been characterized as an open channel blocker of various nAChR subtypes (Neher, E. and J. H. Steinbach *J. Physiol* [1978] 277:135–176; Pascual, J. M. and A. Karlin *J. Gen. Physiol.* [1998] 112(5):611–621; Horn, R. et al., *Science* [1980] 210(4466):205–207; Francis, M. M. et al., *Biophys. J.* [1998] 74(5):2306–2317; Wilson, G. Karlin *Proc. Natl. Acad. Sci. USA* [2001] 98(3): 1241–1248) (3, 12–15). Tetracaine has been shown to have both competitive and noncompetitive effects on nAChR function. When functioning as a noncompetitive antagonist, tetracaine appears to have comparable affinity for receptors in the resting and open states (Middleton, R. E. et al., *Mol. Pharmacol.* [1999] 56(2):290–299; Takayama, H. et al., *J. Pharmacol. Exp. Ther.* [1989] 251(3):1083–1089; Papke, R. L. and R. E. Oswald *J. Gen. Physiol.* [1989] 93:785–811; Blanton, M. P. et al., *J. Biol. Chem*[2000] 275(5): 3469–3478; Gallagher, M. J. and J. B. Cohen *Mol. Pharmacol.* [1999] 56(2):300–307). Therefore, these two agents should serve as effective probes for channel-associated sites and in fact may distinguish between sites associated with different forms of channel blockade. The fact that the residual inhibition produced by DMXB and nicotine was unperturbed by the binding of either QX-314 or tetracaine would argue against the idea that these agonists produce that inhibition by binding to the same channel-associated site recognized by the local anesthetics.

Furthermore, the observation that protection from inhibition was provided by a drug which lacks intrinsic inhibitory activity suggests that the binding site protected by TC-2403 is unlikely to be a site within the conduction pathway (i.e. an open channel block site), or TC-2403 itself would have had inhibitory effects. An alternative interpretation therefore is that the agonists are working at a proposed allosteric regulatory site (Arias, H. R. *J. Neurosci. Res.* [1996] 44(2): 97–105; Rozental, R. et al., *J. Pharmacol Exp. Ther.* [1989] 249(1):123–130; Yost, C and B. A. Dodson *Cell Mol. Neurobiol.* [1993] 13(2):159–172; Min, C. K. and G. A. Weiland *Brain Res.* [1992] 586(2):348–351), the accessibility of which is regulated by gating.

Since TC-2403 can protect receptor function from the long-term inhibition by mixed agonists/antagonists, TC-2403 may bind to an allosteric site also recognized by other agonists but not promote the inhibition of function through that binding. As shown in FIGS. 3A–3D, TC-2403 is an effective activator of α3β4(6'F10'T) receptors, but unlike ACh, TC-2403 acts to prevent rather than promote DMXB-induced inhibition. This would indicate that the protective effects of TC-2403 are not associated with its binding to the activation sites (where it behaves like ACh) but rather to different sites where the other agonists promote inhibition but where TC-2403 does not. This would be most consistent with an allosteric binding site, since as noted above, it seems unlikely that TC-2430 would bind to a site within the conduction pathway and not inhibit function. However, since the effects of the inhibitory agonists (i.e.

ACh, DMXB and nicotine) do appear to be voltage dependent, if they are associated with binding to an allosteric site, then it may be the case that the conformation or accessibility of such a site is influenced by gating and/or membrane voltage.

It appears that a specific sequence in the TM2 domain can regulate both the sensitivity of specific nicotinic receptor subtypes to channel blocking agents and effects at sites outside of the ion channel conduction pathway, presumably by affecting gating-dependent conformational changes in the receptor. This effect of beta subunit TM2 sequence on gating-dependent conformational changes is consistent with our previous report on the regulation of voltage-independent use-dependent inhibition by BTMPS (Francis, M. M. et al., *Biophys. J.* [1998] 74(5):2306–2317). While the 6'/10' mutation decreases the inhibitory effects of BTMPS at sites outside the ion channel, these mutations increase inhibition by selected agonists and shift the affinity of tetracaine away from a channel associated site and toward the activation binding site.

EXAMPLE 6
Evaluation of Compounds for Agonist, Antagonist, or Mixed Agonist/Antagonist nAChR Activity and Nicotinic Specificity Binding of the agonist, antagonist, or mixed nAChR agonists/antagonists utilized in the methods and compositions of the present invention to relevant receptor sites can be determined in accordance with the techniques described in U.S. Pat. No. 5,597,919 to Dull et al. Neurotransmitter release can be measured using techniques similar to those previous published (Bencherif et al., J PET [1996] 279:1413–1421). The determination of the interaction of the compounds with muscle receptors can be carried out in accordance with the techniques described in U.S. Pat. No. 5,597,919 to Dull et al. For example, the maximal activation for individual compounds can be determined as a percentage of the maximal activation induced by (S)-(−)-nicotine. Preferable compounds have the capability to activate human CNS receptors without activating muscle-type nicotinic acetylcholine receptors. Therefore, at certain levels, preferred compounds show CNS effects to a significant degree but do not show undesirable muscle effects to any significant degree. The determination of the interaction of the compounds with ganglionic receptors can be carried out in accordance with the techniques described in U.S. Pat. No. 5,597,919 to Dull et al. The measurement and characterization of nAChR inhibition exhibited by a given compound applied alone, and when co-applied with metanicotine, can be determined using the methods described herein (e.g., Examples 1–5).

What is claimed is:

1. A method for reducing an adverse effect associated with administration of 3-[2,4-dimethoxybenzylidene]-anabaseine (GTS-21), wherein said method comprising co-administering metanicotine or a pharmaceutically acceptable salt thereof, with 3-[2,4-dimethoxybenzylidene]-anabaseine (GTS-21) or a pharmaceutically acceptable salt thereof, to a patient in need thereof.

2. The method, according to claim 1, wherein the metanicotine, or pharmaceutically acceptable salt thereof, and the 3-[2,4-dimethoxybenzylidene]-anabaseine (GTS-21), or pharmaceutically acceptable salt thereof, are administered to the patient simultaneously.

3. The method, according to claim 1, wherein the metanicotine, or pharmaceutically acceptable salt thereof, and the 3-[2,4-dlznethoxybenzylidene]-anabaseine (GTS-21), or pharmaceutically acceptable salt thereof, are administered to the patient simultaneously and in the form of a pharmaceutical composition.

4. The method, according to claim 1, wherein the patient is suffering from the neurological condition selected from the group consisting of Alzheimer's disease, Parkinson's disease, Huntington's choren, tardive dyskinesia, hyperkinesias, mania, attention deficit disorder, attention deficit hyperactivity disorder, sleep-wake disorder, chronic-fatigue syndrome, tremor, epilepsy, neuropathic pain, addiction, anxiety, dyslexia, schizophrenia, obsessive-compulsive disorder, Tourette's syndrome and a combination thereof.

5. The method, according to claim 1, wherein the route of administration is selected from the group consisting of intravenous, oral, and intra-nasal.

6. The method, according to claim 1, wherein the metanicotine, or pharmaceutically acceptable salt thereof, and the 3-[2,4-dimethoxybenzylidene]-anabaseine (GTS-21), or pharmaceutically acceptable salt thereof, administered to the patient do not cause an adverse side effect in the patient which is normally associated with administration of the -3-[2,4-dimethoxybenzylidene]-anabaseine (GTS-21) alone, or wherein the metanicotine, or pharmaceutically acceptable salt thereof, and the 3-[2,4-dimethoxybenzylidene]-anabaseine (GTS-21) administered to the patient cause an adverse side effect in the patient which is normally associated with administration of the 3-[2,4-dimethoxybenzylidene]-anabaseine (GTS-21) alone, but of decreased intensity.

7. The method, according to claim 1, wherein the metanicotine, or pharmaceutically acceptable salt thereof, and the 3-[2,4-dimethoxybenzylidene]-anabaseine (GTS-21), or pharmaceutically acceptable salt thereof, are administered in amounts sufficient to penetrate the blood-brain barrier.

* * * * *

UNITED STATES PATENT AND TRADEMARK OFFICE
CERTIFICATE OF CORRECTION

PATENT NO. : 6,852,741 B2
DATED : February 8, 2005
INVENTOR(S) : Roger L. Papke

It is certified that error appears in the above-identified patent and that said Letters Patent is hereby corrected as shown below:

Title page,
Item [57], ABSTRACT,
Line 6, "antagonists" should read -- antagonist --.

Column 1,
Line 60, "a subunits" should read -- $\alpha$ subunits --.

Column 5,
Line 62, "L3 P4(6'F10'T)" should read -- $\alpha 3\beta 4(6'F10'T)$ --.

Column 7,
Line 25, "dimetboxybenzylidene" should read -- dimethoxybenzylidene --.

Column 12,
Lines 20-21, "AspLys     should read -- AspLys
            20'"                    20' --.

Column 18,
Line 19, "G. Karlin" should read -- G. and A. Karlin --.
Line 48, "Yost, C" should read -- Yost, C.S. --.

Column 21,
Line 15, "dlznethoxybenzylidene" should read -- dimethoxybenzylidene --.

UNITED STATES PATENT AND TRADEMARK OFFICE
CERTIFICATE OF CORRECTION

PATENT NO. : 6,852,741 B2
DATED : February 8, 2005
INVENTOR(S) : Roger L. Papke

It is certified that error appears in the above-identified patent and that said Letters Patent is hereby corrected as shown below:

Column 22,
Line 14, "(GTS-21) administered" should read -- (GTS-21), or pharmaceutically acceptable salt thereof, administered --

Signed and Sealed this

Nineteenth Day of July, 2005

JON W. DUDAS
*Director of the United States Patent and Trademark Office*

```
SEQUENCE LISTING

<160> NUMBER OF SEQ ID NOS: 3
<210> SEQ ID NO 1
<211> LENGTH: 25
<212> TYPE: PRT
<213> ORGANISM: Rattus norvegicus

<400> SEQUENCE: 1

Val Thr Leu Cys Ile Ser Val Leu Leu Ser Leu Thr Val Phe Leu Leu
1               5                   10                  15

Val Ile Thr Glu Thr Ile Pro Ser Thr
            20                  25

<210> SEQ ID NO 2
<211> LENGTH: 25
<212> TYPE: PRT
<213> ORGANISM: Rattus norvegicus

<400> SEQUENCE: 2

Met Thr Leu Cys Ile Ser Val Leu Leu Ala Leu Thr Phe Phe Leu Leu
1               5                   10                  15

Leu Ile Ser Lys Ile Val Pro Pro Thr
            20                  25

<210> SEQ ID NO 3
<211> LENGTH: 25
<212> TYPE: PRT
<213> ORGANISM: Rattus norvegicus

<400> SEQUENCE: 3

Met Gly Leu Ser Ile Phe Ala Leu Leu Thr Leu Thr Val Phe Leu Leu
1               5                   10                  15

Leu Leu Ala Asp Lys Val Pro Glu Thr
            20                  25
```